US010165956B2

(12) United States Patent
Jacofsky et al.

(10) Patent No.: US 10,165,956 B2
(45) Date of Patent: Jan. 1, 2019

(54) COMPARTMENT SYNDROME MONITORING SYSTEMS AND METHODS

(71) Applicant: TCI3—Pressure Applications, LLC, Phoenix, AZ (US)

(72) Inventors: Marc C. Jacofsky, Phoenix, AZ (US); David J. Jacofsky, Peoria, AZ (US); John P. Peeters, Williamsburg, VA (US)

(73) Assignee: TCI3—Pressure Applications LLC, Phoenix, AZ (US)

( * ) Notice: Subject to any disclaimer, the term of this patent is extended or adjusted under 35 U.S.C. 154(b) by 308 days.

(21) Appl. No.: 15/130,625

(22) Filed: Apr. 15, 2016

(65) Prior Publication Data

US 2016/0331253 A1 Nov. 17, 2016

Related U.S. Application Data

(63) Continuation of application No. 12/832,767, filed on Jul. 8, 2010, now Pat. No. 9,314,175.

(51) Int. Cl.
*A61B 5/00* (2006.01)
*A61B 5/03* (2006.01)
*A61B 5/07* (2006.01)

(52) U.S. Cl.
CPC ............ *A61B 5/036* (2013.01); *A61B 5/0031* (2013.01); *A61B 5/03* (2013.01); *A61B 5/076* (2013.01);
(Continued)

(58) Field of Classification Search
CPC ........... A61B 5/03; A61B 5/031; A61B 5/033; A61B 5/036–5/038
See application file for complete search history.

(56) References Cited

U.S. PATENT DOCUMENTS 4,711,248 A 12/1987 Steuer et al.
4,817,629 A 4/1989 Davis
(Continued)

FOREIGN PATENT DOCUMENTS

JP 2005-511184 4/2005
JP 2006-289081 10/2006
(Continued)

OTHER PUBLICATIONS

International Preliminary Report on Patentability for International Application No. PCT/US2011/043219, The International Bureau of WIPO, Geneva, Switzerland, dated Jan. 17, 2013.
(Continued)

*Primary Examiner* — Max Hindenburg
(74) *Attorney, Agent, or Firm* — Sterne, Kessler, Goldstein & Fox P.L.L.C.

(57) ABSTRACT

Embodiments of a compartment monitor that can be implanted and left in situ to continuously (or semi-continuously) measure compartment pressures are presented. An exemplary monitor includes a pressure sensor adapted to be implanted in a compartment, a transmitter external to the compartment and coupled to the pressure sensor, and a receiver in communication with the transmitter to receive and process pressure data received from the transmitter. The monitor may also be configured to transmit measured pressure data to a networkable device. The networkable device can then communicate the patient's status and condition to a healthcare provider through a local area network (LAN) or wide area network (WAN). This communication allows the healthcare provider to remotely monitor a patient. The networkable device, or associated computing system, can record and display trends in the pressure data over time, and log the data to the patient's electronic health records.

20 Claims, 17 Drawing Sheets

(52) U.S. Cl.
CPC .......... *A61B 5/4519* (2013.01); *A61B 5/6828* (2013.01); *A61B 5/6833* (2013.01); *A61B 5/6853* (2013.01); *A61B 5/7275* (2013.01); *A61B 5/7282* (2013.01); *A61B 5/746* (2013.01); *A61B 2562/0247* (2013.01); *A61B 2562/168* (2013.01)

(56) References Cited

U.S. PATENT DOCUMENTS

| | | |
|---|---|---|
| 4,858,620 A | 8/1989 | Sugarman et al. |
| 6,942,634 B2 | 9/2005 | Odland |
| 6,980,852 B2 | 12/2005 | Jersey-Willuhn et al. |
| 7,148,803 B2 | 12/2006 | Bandy et al. |
| 7,256,708 B2 | 8/2007 | Rosenfeld et al. |
| 7,461,972 B2 | 12/2008 | Cohen |
| 2003/0004403 A1 | 1/2003 | Drinan et al. |
| 2005/0061079 A1 | 3/2005 | Schulman |
| 2005/0288596 A1 | 12/2005 | Eigler et al. |
| 2005/0288722 A1 | 12/2005 | Eigler et al. |
| 2006/0015025 A1 | 1/2006 | Johnstone |
| 2006/0189889 A1 | 8/2006 | Gertner |
| 2006/0290496 A1 | 12/2006 | Peeters |
| 2007/0015994 A1 | 1/2007 | Hong et al. |
| 2007/0109117 A1 | 5/2007 | Heitzmann et al. |
| 2008/0146946 A1 | 6/2008 | Montegrande et al. |
| 2008/0154101 A1 | 6/2008 | Jain et al. |
| 2008/0208011 A1 | 8/2008 | Shuler |
| 2009/0099436 A1 | 4/2009 | Brister et al. |
| 2009/0171413 A1 | 7/2009 | Zenati et al. |
| 2009/0184821 A1 | 7/2009 | Kuris et al. |
| 2009/0209904 A1 | 8/2009 | Peeters |
| 2010/0106140 A1 | 4/2010 | Odland et al. |

FOREIGN PATENT DOCUMENTS

| | | |
|---|---|---|
| JP | 2007-229490 | 9/2007 |
| JP | 2009-213886 | 9/2009 |
| JP | 2010-520773 | 6/2010 |

OTHER PUBLICATIONS

Extended European Search Report for European Patent Application No. 11804354.6, dated Oct. 22, 2014, 7 pages.
Official Action for Japanese Appl. No. 2013-518834, with English-language translation, dated Feb. 23, 2015, 8 pages.
Official Action for European Appl. No. 11 804 354.6, dated Sep. 21, 2015, 5 pages.

COMPARTMENT SYNDROME MONITORING SYSTEMS AND METHODS

CROSS-REFERENCE TO RELATED APPLICATIONS

This application is a continuation of U.S. application Ser. No. 12/832,767, which has a filing date of Jul. 8, 2010, the disclosure of which is hereby incorporated by reference in its entirety.

FIELD

The present invention is related to systems and methods for diagnosing compartment syndrome. More specifically, the present invention is related to a partially implantable wireless compartment syndrome monitor.

BACKGROUND

Compartment syndrome is a medical condition where the pressure inside a compartment (i.e., muscle group surrounded by inelastic fascia) rises higher than the pressure in the capillaries of the tissue. Compartment syndrome leads to limited or lost circulation to the region. Compartment syndrome usually occurs after a trauma or injury to the tissues contained within the compartment. Because the fascia does not expand, bleeding or swelling that results from the trauma or injury causes increased pressure within the compartment. Venous pathways in the compartment are then restricted from draining blood and fluid from the injured area, and the pressure within the compartment continues to rise. Continued pressure increases further restrict circulation and eventually lead to the death of the affected tissue (i.e., necrosis). Necrosis will often lead to the loss of limb, and possibly loss of life in severe cases. The most common site for compartment syndrome occurs in the lower leg; specifically, in regions adjacent to the tibia and fibula.

There are four compartments in the lower human leg: the anterior (front), lateral (side next to the fibula), deep posterior (back), and the superficial posterior (back). Any one of these four compartments can yield a compartment syndrome when bleeding or swelling occurs within the compartment. Compartment syndrome can also result from a cast that is too tight, constrictive dressings, pneumatic anti-shock garments, and closure of fascial defects. The clinical conditions that may be associated with compartment syndrome include the management of fractures, soft tissue injuries, arterial injuries, drug overdoses, limb compression situations, burns, post-ischemic swelling, constrictive dressings, aggressive fluid resuscitation, and tight casts.

FIG. 1 illustrates a human leg 100 with fractured bones of the tibia 105 and fibula 110, which can lead to one or more compartment syndromes in the muscles 115 surrounding the bones. The tibia 105 and fibula 110 usually bleed in regions proximate to the physical break regions 120. This bleeding can form a large pool of stagnant blood (i.e., a hematoma). The hematoma can start pressing upon muscles 115, which may be proximate to physical break regions 120. The pressure caused by the hematoma can restrict or stop blood flow into the muscles 115 of a compartment, which leads to compartment syndrome. Normal compartment pressures are under 20 mm Hg. Concern is raised when pressures rise above 20 to 30 mm Hg, and critical intervention is often required above 30 mm Hg.

Traditional methods for diagnosing compartment syndrome include highly invasive and challenging direct pressure-measurement procedures. A needle or trocar is used to access the compartment to conduct an intra-compartmental pressure measurement. Currently, such intra-compartmental pressure measurements are the only objective and reliable diagnostic tool. The diagnosis and treatment of compartment syndrome, however, can cause significant morbidity and increase the risk for infection. Therefore, inaccurate and elevated pressure readings are a very difficult and potentially dangerous pitfall.

Current needle-based pressure measuring methods are also undesirable because they only provide a snap-shot of data at an instant of time. In other words, the needle-based pressure measuring method only provides the medical practitioner with one data point for a particular time. Once pressure is read by the medical practitioner, he or she usually removes the needle from the patient. The data obtained from a single measurement in time gives no information concerning the pressure trend, and the direction the intra-compartmental pressure is moving. The collection of single data points over long periods of time is usually not very helpful because pressures within a compartment, as well as the patient's blood pressure, can change abruptly (e.g., within minutes). Further, the pain associated with the needle-based pressure measuring method restricts the medical practitioner from taking a pressure reading within a few minutes of a previous reading.

The diagnosis of compartment syndrome before the situation becomes critical is difficult, and a missed diagnosis or false positive diagnosis can have significant consequences for the patient. Treatment of compartment syndrome typically requires a fasciotomy, which is invasive, painful, complicated, and increases risk of infection and morbidity. Therefore, it is desirable to monitor the pressure in the compartment to properly and continuously assess when surgical intervention becomes absolutely necessary.

Furthermore, these traditional methods require the patient to remain in the treatment facility if continuous monitoring of compartment pressure is required. This increases the cost of treatment for the facility and the cost and inconvenience to the patient. Therefore, methods for accurately monitoring and tracking compartment pressure remotely, for example at a patient's home, are desirable.

For more information on compartment syndrome, and diagnostic and treatment methods, reference is made to the following U.S. patent and U.S. published applications, all of which are incorporated herein by reference in their entirety: U.S. Pat. Nos. 4,711,248; 4,817,629; 4,858,620; 6,942,634; and 2008/0208011. Further, reference is made to the following U.S. patents and/or publications, all of which are incorporated herein by reference in their entirety, and the subject matter of which may be related to the present invention: U.S. Pat. Nos. 6,980,852; 7,148,803; 7,256,708; 7,461,972; and 2006/0290496.

BRIEF DESCRIPTION OF THE FIGURES

The accompanying drawings, which are incorporated herein, form part of the specification and illustrate embodiments of compartment syndrome monitoring and diagnostic systems, sensors, and methods. Together with the description, the drawings further serve to explain the principles of, and to enable a person skilled in the relevant art(s) to make and use, the systems and methods described herein. In the drawings, like reference numbers indicate identical or functionally similar elements.

DETAILED DESCRIPTION

Figure 1:
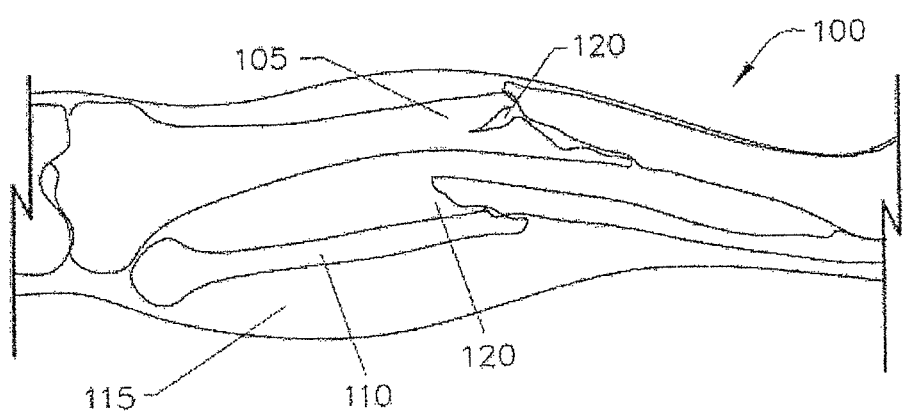
FIG. 1 illustrates a human leg with fractured bones of the tibia and fibula.

The following detailed description of compartment syndrome monitoring and diagnostic systems, sensors, and methods refers to the accompanying drawings that illustrate exemplary embodiments. Unless otherwise noted, all embodiments and examples should be considered prophetic examples. Other embodiments are possible. Modifications can be made to the embodiments described herein without departing from the spirit and scope of the present invention. Therefore, the following detailed description is not meant to be limiting. Further, it would be apparent to one of skill in the art that the systems and methods described below can be implemented in many different embodiments of hardware, software, and/or firmware. Any actual hardware, software, and/or firmware described are not meant to be limiting.

Presented herein are embodiments of a compartment monitor that can be implanted and left in situ to continuously (or semi-continuously) measure compartment pressures. These monitors can be used to measure compartment pressure for extended time periods, for example, over 24-48 hours. The monitors are also configured to transmit measured pressure data to a networkable device (e.g., a laptop computer, personal digital assistant (PDA), or cell phone) over a communication link such as a wireless link. The networkable device can then communicate the patient's status and condition to a healthcare provider (e.g., nurses, doctors, and other hospital personnel) through a local area network (LAN) or wide area network (WAN). This communication allows the healthcare provider to remotely monitor a patient. The networkable device, or associated computing system, can record and display trends in the pressure data over time, and log the data to the patient's electronic health records. The networkable device, or associated computing system, can also compare the pressure data to the patient's diastolic blood pressure, and calculate clinically important gradients in real time.

In addition to monitoring compartment pressure, the monitors presented herein can also be useful for monitoring intracranial pressure after closed head injury, brain infection, etc. or the pressure within any lumen or enclosed area of the body.

The compartment pressure monitors described herein include at least one pressure sensor. In one embodiment, the pressure sensor is tied directly to a device that includes a signal conditioner and a processor for direct read-out on the sensing device. In another embodiment the pressure sensor is integrated with a radio-frequency identification (RFID) device that has the capability of transmitting the measured pressure data to an interrogating device. The RFID device may be passive, pass-active (battery assisted), or fully active (battery dependent) depending upon the frequency of desired reads, the estimated distance of the interrogating device from the RFID device, and the power consumption needs of the RFID device. In alternative embodiments, the pressure sensor is integrated with Bluetooth® radio technology, ZigBee® radio technology, or other radios compatible with wireless devices such as cell phones.

Figure 2:
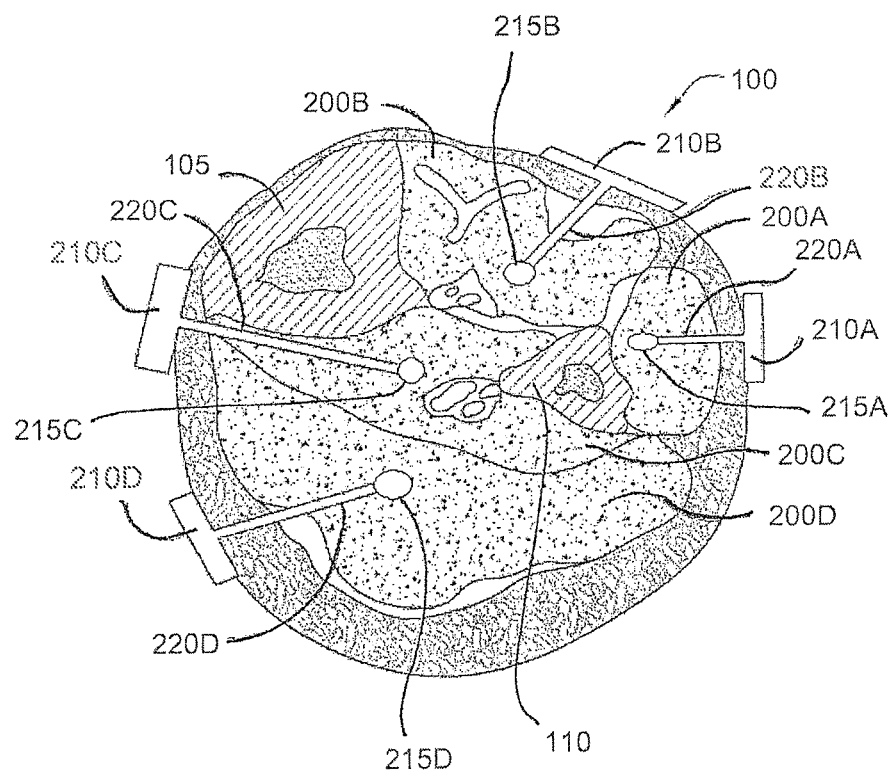
FIG. 2 illustrates a cross-sectional view of a human leg, illustrating the four major compartments, and schematically depicting four compartment monitors, according to one embodiment presented herein.

In an embodiment, the pressure sensor of the compartment monitor resides outside the body, while being in fluid communication with a flexible bulb inside of the compartment. An example of this embodiment is depicted in FIG. 2. FIG. 2 illustrates a cross-sectional view of a human leg 100, illustrating the four major compartments 200A, 200B, 200C, and 200D, and schematically depicting four compartment monitors 210A, 210B, 210C, and 210D. As illustrated, compartment monitors 210A-D include a flexible, fluid-filled bulb 215A-D implanted into each compartment 200A-D. In this embodiment, the small flexible bulb 215A-D, sac, balloon, or a similar vessel is filled with an incompressible fluid and is connected to a thin tube 220A-D. The thin tube 220A-D is inelastic and is filled with an incompressible fluid. The thin tube 220A-D is in fluid communication with the pressure sensor, which resides outside the body and is preferably built into a skin patch that contains a radio-frequency (RF) device.

The bulb 215 may be manufactured from any flexible medical grade plastic or composite such as silicone, rubber, latex, nitrile, or similar material. The tube 220 may be composed of a similar but stiffer material (Polyethylene, TEFLON, DELRIN, etc.) which can be covered in a braided metal layer if necessary to increase resistance to deformation when the pressure changes, or to ensure the tube is strong enough to withstand tugging when the implant is removed. In one embodiment, the bulb-tube system is prepared as a sealed unit that is assembled at the manufacturing facility; instead of at a hospital. Controlled manufacturing and preparation prevents air bubbles in the bulb-tube fluid communication system, and thus ensures accurate relaying of the pressure to the external pressure sensor.

The bulb 215, and attached tube 220, can be inserted into the muscle compartment such that the bulb 215 resides in the area of interest for pressure monitoring and the thin tube 220 exits the skin and attaches to the pressure sensor. A change in compartment pressure will increase pressure on the walls of the bulb and thereby force fluid out into the tube. As such, the fluid in the closed bulb-tube system contacts the pressure sensor directly, and thereby communicates changes in pressure occurring on the bulb inside the compartment. Since the tube is inelastic, and the fluid inside the tube is incompressible, the corresponding pressure change at the bulb will be seen at the pressure sensor. As such, changes in pressure in the compartment are registered at the pressure sensor on the surface of the patient's skin.

A correction factor can be introduced to account for factors such as: the volume of fluid in the flexible bulb, the diameter of the tube through which the pressure will be sensed, the location or position on the body, and the temperature of the system, patient, or ambient temperature. The bulb-tube system has several advantages including: reduction in cost because the pressure sensor and associated electronics need not be miniaturized for direct implantation; and simplification of the pressure sensor because the sensor itself is not implanted within the body, the sensor is not submerged within an aqueous environment and the electronics are not subject to Food and Drug Administration (FDA) guidelines for an implantable device.

At the surface of leg 100, the pressure sensor is coupled to a device such as an RFID device or other similar wireless device. The device can be used to record and/or transmit the measured pressure data to an external reader. The device may additionally include an integrated or external temperature sensor or additional sensors to measure or determine one or more correction factors.

FIG. 2 is presented for illustrative purposes only. Any of the compartment monitors disclosed herein can be exchanged for the monitors 210A-D shown in FIG. 2.

Figure 3:
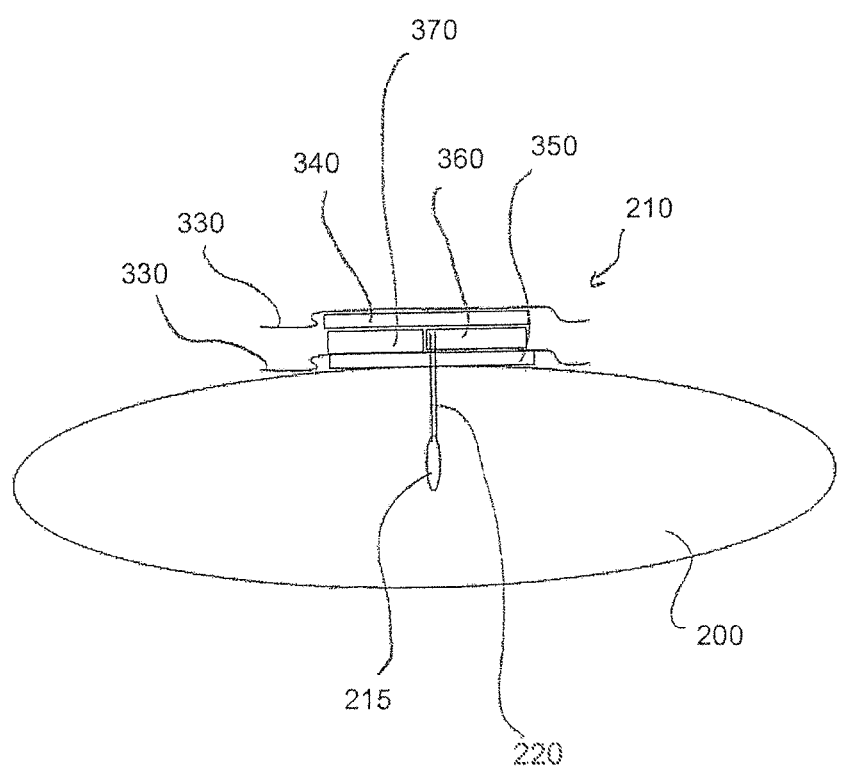
FIG. 3 is a schematic view of a compartment monitor in accordance with one embodiment presented herein.

FIG. 3 is a schematic view of an exemplary compartment monitor 210, in accordance with one embodiment presented herein. As shown in FIG. 3, flexible fluid-filled bulb 215 is implanted into compartment 200. Inelastic tube 220 is attached between flexible bulb 215 and a fluid-pressure sensor 360, which is external to the compartment 200. Pressure changes within compartment 200 affect the volume of fluid within bulb 215. When the pressure within compartment 200 increases, fluid within bulb 215 is pushed up into tube 220. Because tube 220 is inelastic, and the fluid within bulb 215 and tube 220 is incompressible, the pressure change within compartment 200 is registered at pressure sensor 360. In the embodiment shown, the pressure data is then communicated to an RFID device coupled to the pressure sensor. In the embodiment shown, pressure sensor 360 and RFID device are powered by flexible battery 370. As would be appreciated by persons of skill in the art, RFID device and/or pressure sensor may be powered by other techniques. A substrate 330 (e.g., a layer of an adhesive bandage) is used to house and maintain the RFID device, flexible battery 370, and fluid-pressure sensor 360. Additional external sensors may further be included in the adhesive bandage material. Sterile gauze 350 may be present in between substrate 330 and the surface of the skin.

Figure 4:
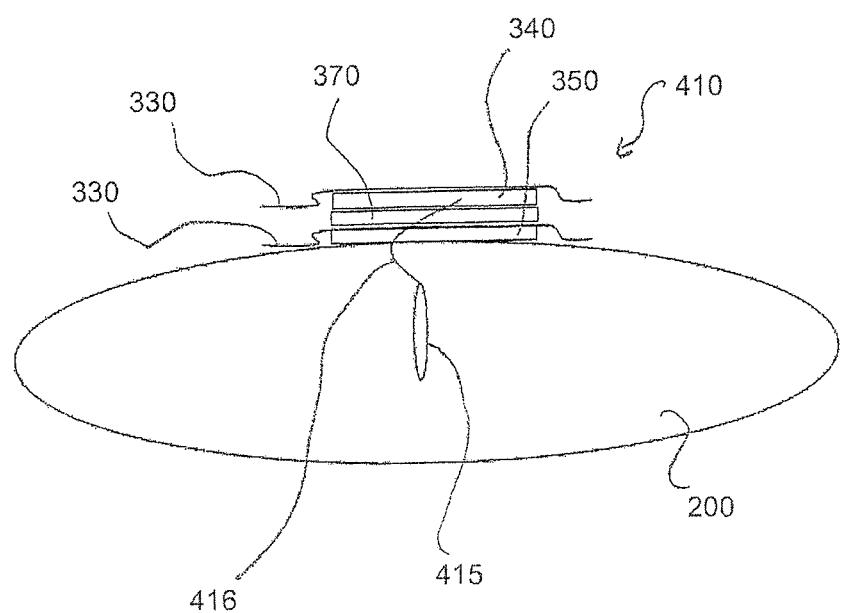
FIG. 4 is a schematic view of a compartment monitor in accordance with an alternative embodiment presented herein.

In a further embodiment, a pressure sensor is inserted into a muscle compartment, neurocranium, or other closed bodily space, via a needle or trocar. FIG. 4 is a schematic view of a compartment monitor 410 having a pressure monitor inserted into a compartment, according to embodiments of the present invention. In the embodiment shown in FIG. 4, an implantable in-dwelling pressure sensor is implanted into the compartment 200.

In one embodiment, the pressure sensor is a microelectromechanical system (MEMS) sensor on the order of 1 mm. The relatively small size of a MEMS pressure sensor allows easy insertion into the tissue. Such MEMS sensors use a change in resistance, change in capacitance, change in voltage, or a piezoelectric effect to convert changes in pressure on a sensing membrane to a voltage, current, or frequency change in the output signal. The pressure sensor can remain in the body for a prescribed period of time (generally 24-48 hours for compartment syndrome monitoring, but possibly longer for intracranial pressure monitoring).

The pressure sensor is coupled to a wire 416 that exits the compartment and skin and is coupled to an RF device 340 on a surface patch or bandage. In embodiments, a battery 370 is coupled to the RF device 340 to provide power. The RF device 340 powers the sensor 415, and interprets or relays the data from the pressure sensor to an interrogating reader. The pressure sensor can be removed by pulling the lead wire away from the skin.

A substrate 330 is used to maintain the RF device 340 and battery 370 on the surface of the skin or tissue of the patient. Sterile gauze 350 is used between the electronic components and the surface of the skin or tissue. For example, the substrate 330 may be used on the surface of a limb or cranium of a patient.

Figure 5:
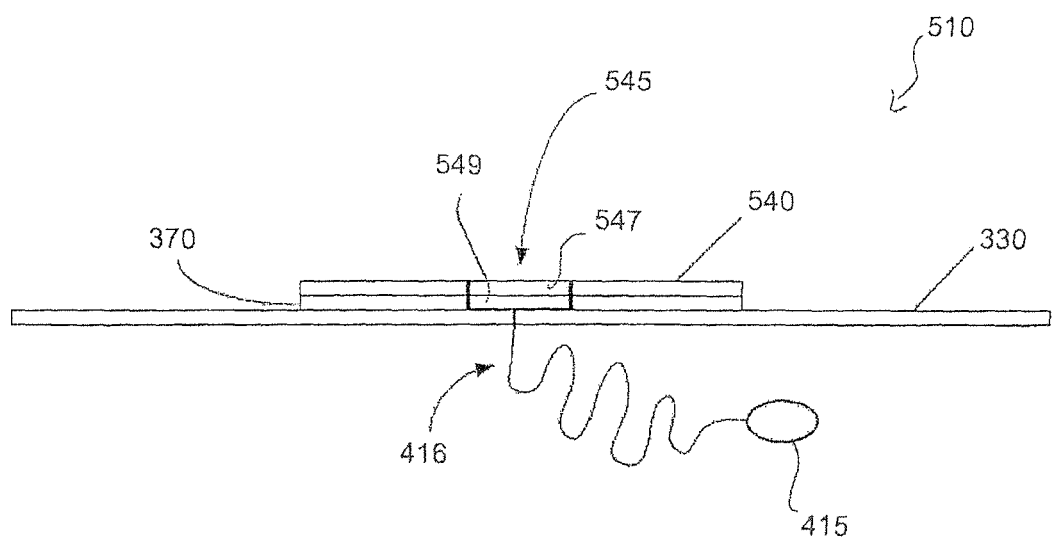
FIG. 5 is a schematic view of a compartment monitor in accordance with an alternative embodiment presented herein.

FIG. 5 is a schematic view of a compartment monitor 510 in accordance with an alternative embodiment presented herein. Like the embodiment shown in FIG. 4, compartment monitor 510 includes an implantable in-dwelling MEMS pressure sensor 415. A wire or tether 416 electrically couples the MEMS pressure sensor 415 to a RF device 545. RF device 545 is described in further detail below. Unlike the device 340 of FIG. 3, the RF device 545 of FIG. 5 includes both RFID circuitry 547 and a pressure sensor interface 549. The pressure sensor interface 549 receives pressure data from the MEMS pressure sensor 415 and processes that data for the RFID circuitry 547. RF device 545 may be powered by flexible battery 370. As would be appreciated by persons of skill in the art, RFID device and/or pressure sensor may be powered by other techniques. Compartment pressure data is transmitted to an external RFID reader (not illustrated) through an RF antenna 540. The RF device 545, flexible battery 370, and antenna, are coupled to or integrated into an adhesive bandage or substrate 330.

Figure 6:
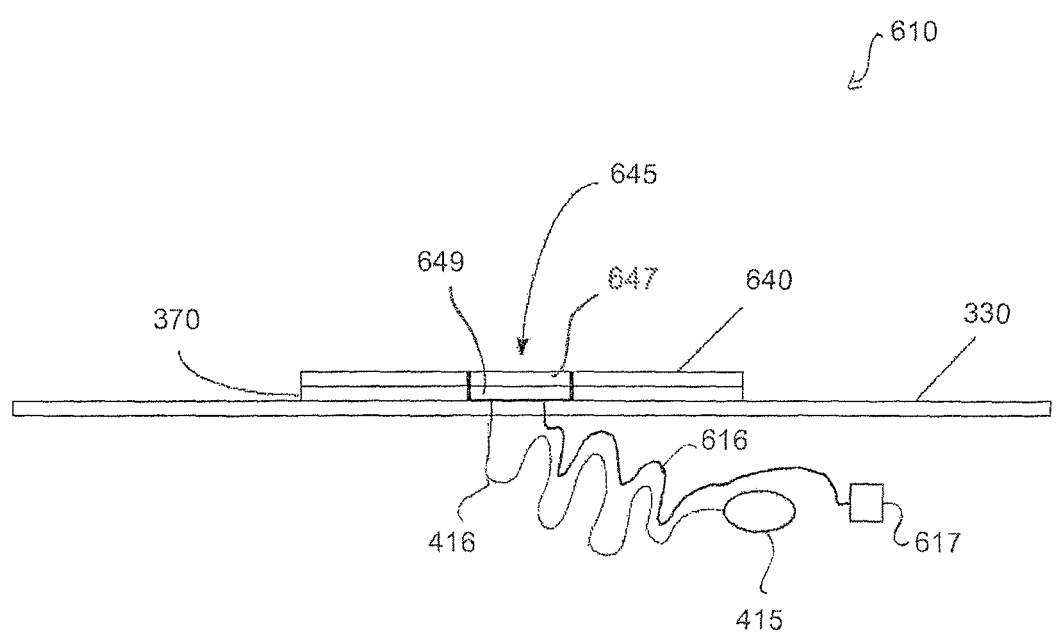
FIG. 6 is a schematic view of a compartment monitor in accordance with an alternative embodiment presented herein.

FIG. 6 is a schematic view of a compartment monitor 610 in accordance with an alternative embodiment presented herein. Similar to the embodiment shown in FIG. 5, compartment monitor 610 includes an implantable in-dwelling MEMS pressure sensor 415 that is electrically coupled to an RF device 645 through a wire or tether 416 via a pressure sensor interface 649. The RF device 645 includes an RFID chip 647. However, compartment monitor 610 further includes an auxiliary sensor 617 that is also implanted within the compartment. Auxiliary sensor 617 is coupled to the RF device 645 through a wire or tether 616. The auxiliary sensor 617 can be used to measure alternative parameters other than pressure in the compartment. For example, auxiliary sensor 617 can be a temperature sensor.

Alternatively, auxiliary sensor 617 can be a pH sensor. Alternatively there can be multiple auxiliary sensors taking additional measurements, as required. The pressure sensor 415 and one or more auxiliary sensors 617 are coupled to the RFID chip 647. RF device 645 is discussed in further detail below. These systems may be powered by a flexible battery 370. As would be appreciated by persons of skill in the art, RFID device and/or pressure sensor may be powered by other techniques. The data collected is transmitted to an external wireless receiver via RE antenna 640. The RE device 645, battery 370, and antenna 640 all rest on an adhesive bandage or substrate 330.

Figure 7:
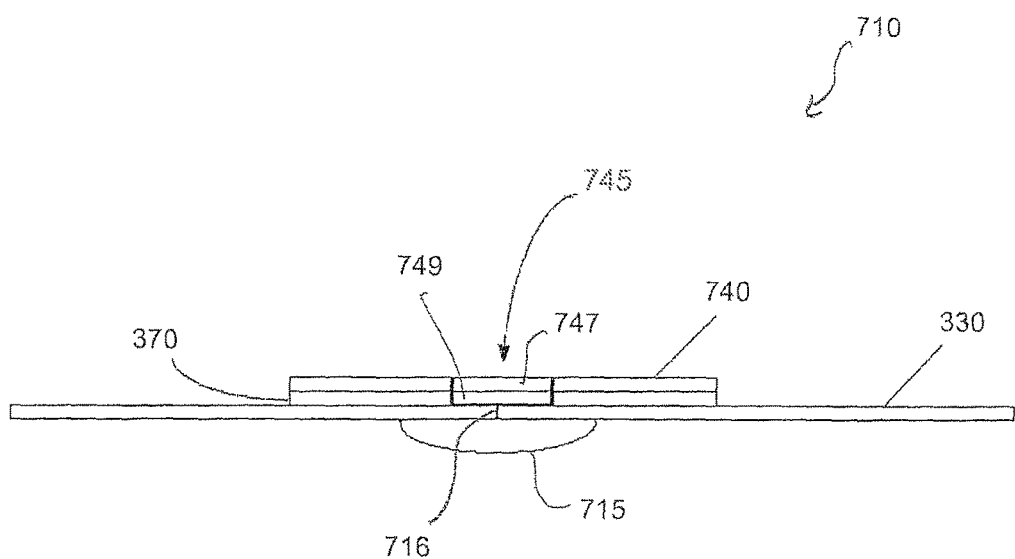
FIG. 7 is a schematic view of a compartment monitor in accordance with an alternative embodiment presented herein.

FIG. 7 is a schematic view of a compartment monitor 710 in accordance with an alternative embodiment presented herein. In the embodiment shown in FIG. 7, the compartment monitor does not include an implantable pressure sensor. Instead the compartment monitor includes an external pressure sensor 715 which rests on the surface of the leg of the patient. As such, compartment monitor 710 can be used and placed in between the leg of a patient and a cast and can be used to determine whether the pressure inside of a cast has exceeded a certain amount. The compartment monitor 710 of FIG. 7 further includes an RF device 745 coupled to the pressure sensor. RF device 745 may further include a sensor interface 749 and an RFID chip 747. Data is communicated from the pressure sensor 715 to the RFID chip 747 through wire or tether 716 and sensor interface 749. RF Device 745 further includes an RF antenna 740. The systems may be powered by flexible battery 370. As would be appreciated by persons of skill in the art, RF device and/or pressure sensor may be powered by other techniques.

Figure 8:
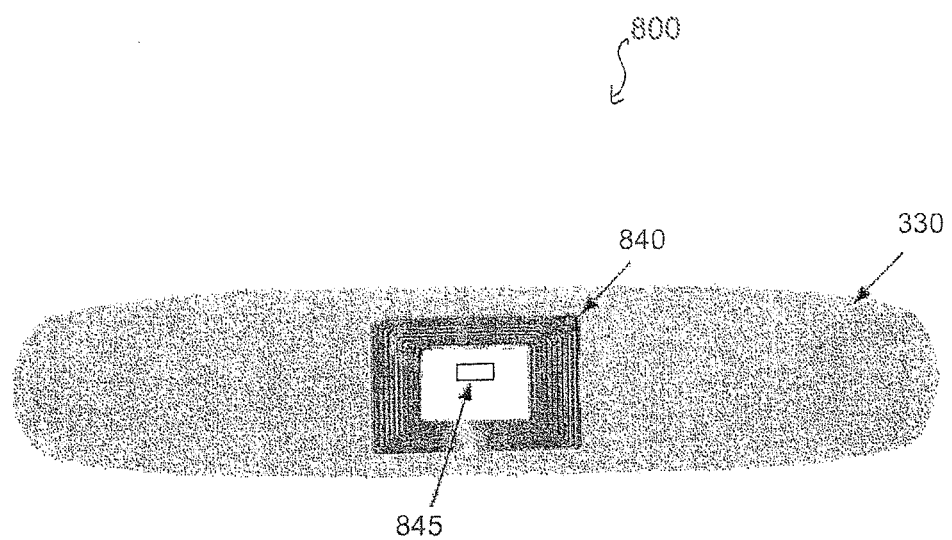
FIG. 8 is a top view of a bandage incorporating a compartment monitor, in accordance with an one embodiment presented herein.

FIG. 8 is a top view of a bandage 800 incorporating a compartment monitor, in accordance with an embodiment presented herein. Bandage 800 includes a substrate 330. The RF devices (and associated antennae) described above may be coupled to the surface of substrate 330. Substrate 330 may include an adhesive material on one surface for affixing the bandage to the skin of the patient. Substrate 330 may further include multiple layers. In this embodiment, the RF device 845 and antenna 840 may be integrated within layers of the substrate 330.

In the embodiment illustrated in FIG. 8, the RF device is placed on top of the substrate 330. In FIG. 8 the bandage is an oval shape, of course the bandage could be any other type of shape. Bandage 800 may be used with any of the compartment monitors described above.

Figure 9:
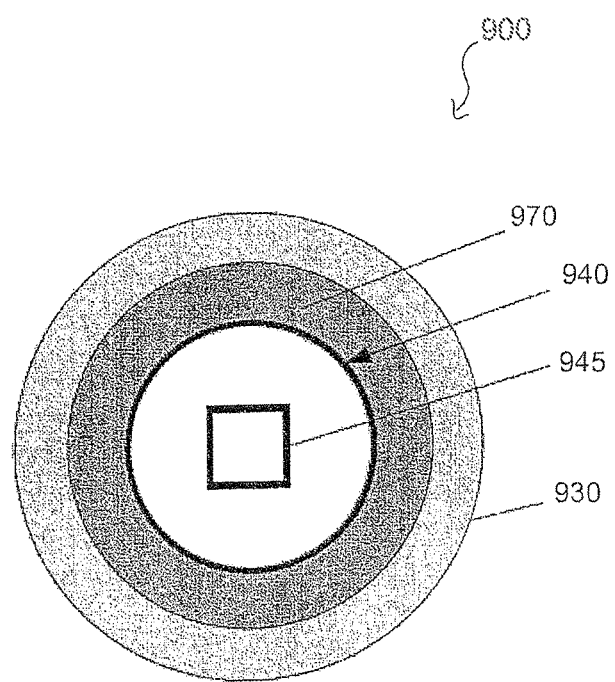
FIG. 9 is a top view of an alternate embodiment of a bandage incorporating a compartment monitor in accordance with an alternative embodiment presented herein.

FIG. 9 is a top view of an alternate embodiment of a bandage incorporating a compartment monitor in accordance with an alternative embodiment presented herein. Bandage 900 has a substrate 930 in a circular shape. Resting on the substrate 930 is a flexible battery 970. Resting on top of the flexible battery is an RF device 945 and antenna 940.

In the embodiments of FIGS. 8 and 9, the compartment pressure monitor is not illustrated. However, the embodiments of FIGS. 8 and 9 may include one or more compartment pressure monitors such as the compartment pressure monitors described herein.

Figure 10:
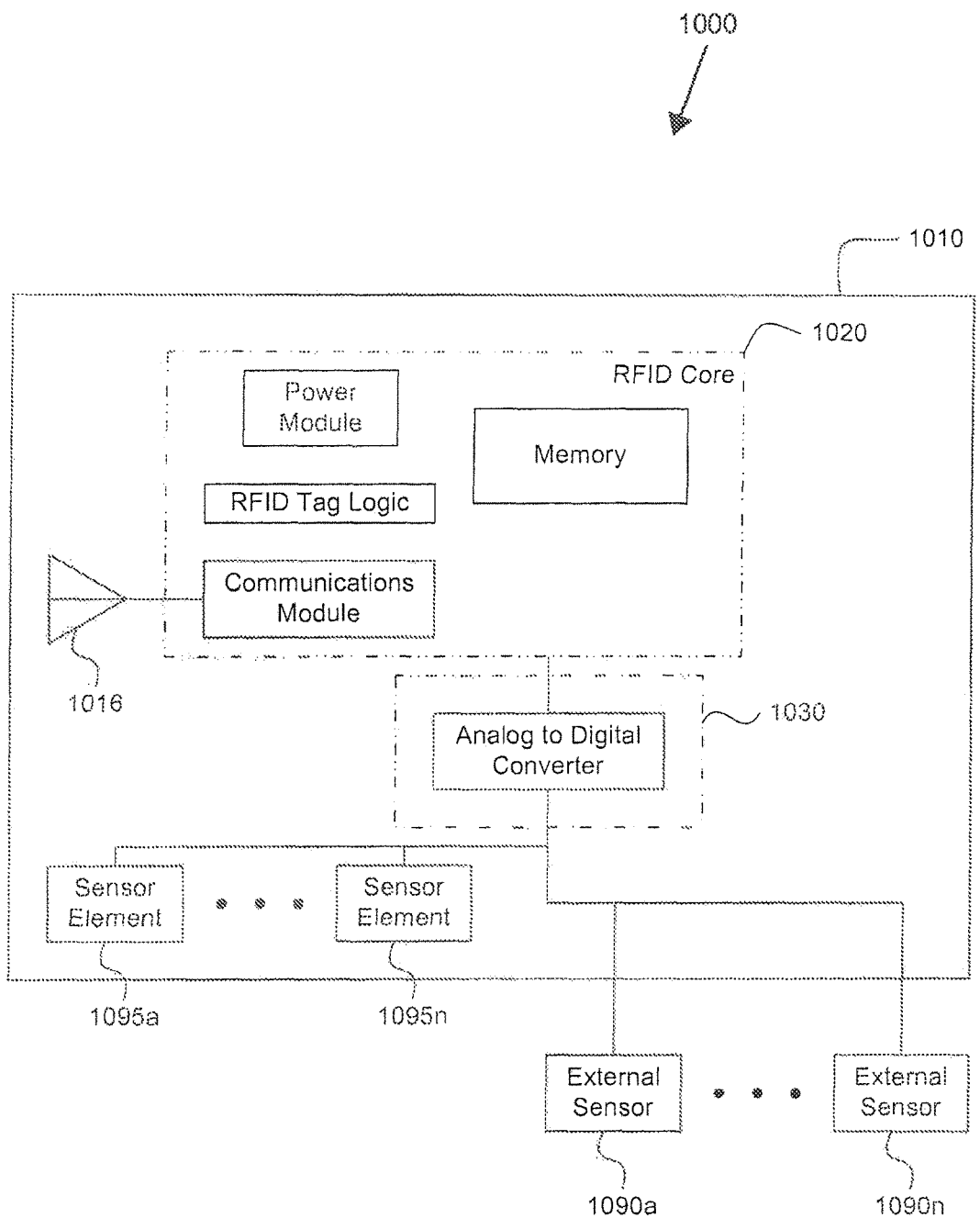
FIG. 10 is a system for monitoring compartment pressure, according to an embodiment of the present invention.

FIG. 10 is a system 1000 for monitoring compartment pressure, according to an embodiment of the present invention. System 1000 includes an RF device 1010 coupled to one or more external sensors 1090. RF device 1010 includes an RF core 1020, an analog to digital converter (ADC) 1030, and one or more antennas 1016. These components are mounted or formed on a substrate. Additionally, the RF core 1020 and/or ADC 1030 may be included in an integrated circuit. RF device 1010 may also include one or more sensor elements 1095, such as sensor elements 1095*a-n*. Sensor elements 1095 may be included in the integrated circuit, on the substrate, external to substrate, or in any combination of the above. As shown in FIG. 10, sensor elements 1095 are included on the substrate. Any compatible sensor element can be used as sensor element 1095.

Sensor elements 1090*a-n* are external to the RF device 1010. External sensors include the sensors (e.g., MEMS sensor) described above for measuring compartment pressure. These external pressure sensors may be coupled to a pressure probe through a wire connector as illustrated in FIGS. 4-6 or an inelastic fluid filled tube as illustrated in FIGS. 2-3. In an alternate embodiment, a fiber optic connection may be used.

Various types of sensor elements can be implemented as integrated sensors 1095 or external sensors 1090. For example, an integrated or external sensor may include a temperature sensor element that generates information indicating ambient temperature, a pH sensor element, or other biological or chemical sensors. The system may include other types of sensor elements or combinations thereof, as would be apparent to persons skilled in the relevant art(s).

Figure 11:
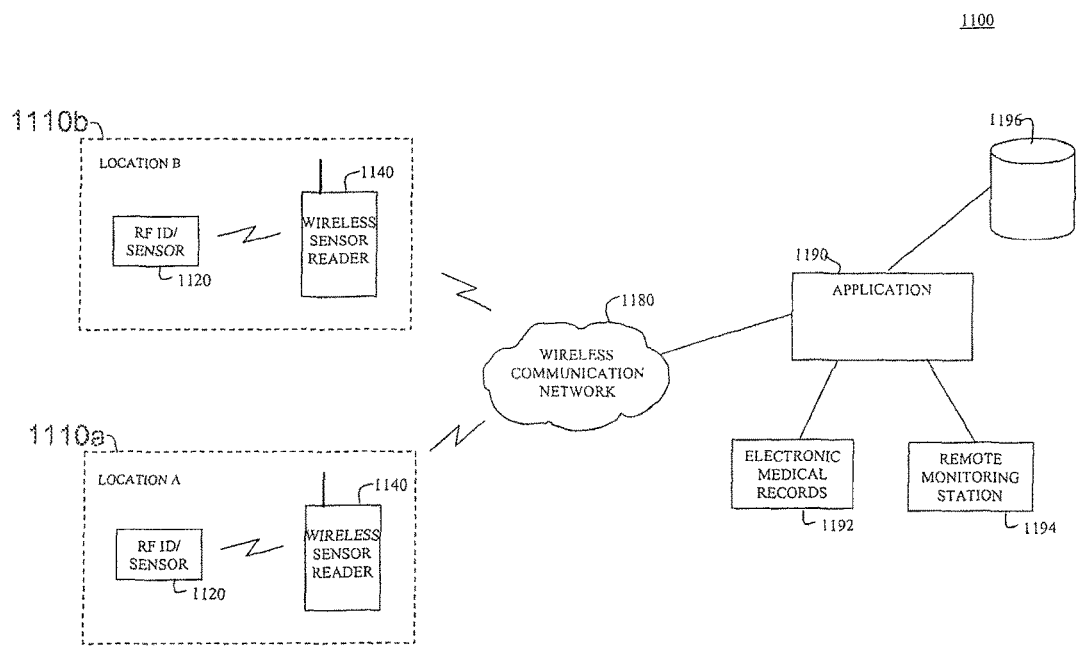
FIG. 11 is a block diagram of an illustrative network 1100 for remotely monitoring one or more orthopedic sensors integrated with RFID devices, according to an embodiment of the present invention.

FIG. 11 is a block diagram of an illustrative network 1100 for remotely monitoring one or more orthopedic sensors integrated with RFID devices, according to an embodiment of the present invention. Network 1100 includes a plurality of remote locations 1110, such as remote locations 1110*a* and 1110*b*. Each remote location 1110 includes an RFID/sensor readers 1140 and one or more RFID device and integrated sensors (RFID/sensor device) 1120. RFID/sensor device 1120 may have one or more devices integrated into the RFID device and one or more external sensors. The wireless RFID/sensor readers 1140 are coupled to a backend application via a communications network 1180. In an embodiment of the present invention, communications network 1180 is a publicly accessible communications network. In another embodiment, communications network 1180 is a private network or a hybrid network including public and private portions. Persons skilled in the relevant art(s) will recognize that various network architectures could be used for communication network 1180.

Wireless RFID/sensor reader 1140 includes logic to read sensor data and RFID tag data transmitted by RFID/sensor device 1120. In an embodiment, wireless RFID/sensor reader 1140 also includes logic to process the received sensor data. Wireless RFID/sensor reader 1140 can be any wireless device capable of communicating via an air interface protocol with RFID/sensor devices 1120. In embodiments of the present invention, wireless RFID/sensor reader 1140 could be a wireless phone, a personal digital assistant (PDA), a computer having wireless communications capabilities, or other type of mobile, handheld, and/or computing device (e.g., an iPad® tablet computer). In further embodiments, wireless RFID/sensor reader 1140 may include global positioning system (GPS) or similar technology to identify the location of the RFID/sensor reader 1140.

In embodiments, wireless RFID/sensor readers 1140 are deployed at different locations. For example, a patient released from a healthcare facility may be given an RFID/sensor reader for monitoring an implanted (or surface) compartment pressure sensor. In this manner, patients can leave the healthcare facility yet receive continuous monitoring to detect any changes in this condition.

According to the present invention, signals are exchanged between the wireless RFID/sensor reader 1140 and RFID/sensor device 1120 according to one or more protocols. In an embodiment of the present invention, reader 1140 and the RFID/sensor devices 1120 communicate via a single protocol for both RFID tag communications and sensor communications. In an alternate embodiment, reader 1140 and RFID/sensor devices 1120 communicate via a first protocol for RFID tag communications and via a second protocol for sensor communications. Examples of protocols used for RFID tag communications include binary tree traversal, HF ISO 15693 and EPC global Gen 2. The present invention is also applicable to any other types of communication protocols between tags and readers otherwise known or yet to be developed.

In an embodiment of the present invention, signals are exchanged between the wireless RFID/sensor reader 1140 and communication network 1180 according to one or more protocols. As can be appreciated by a person skilled in the relevant art(s), the communications protocol used between reader 1140 and communications network 1180 can be any wireless air interface protocol, such as used in IS-41 or GSM wireless communications networks, for example. Additionally, or alternatively, the communications may also be using a standard data communications protocol.

Application 1190 receives sensor data over network 1180, and processes the data. In an embodiment, application 1190 also receives location information for the RFID/sensor reader 1140 (e.g., GPS position data). Furthermore, in an embodiment, the application 1190 may transmit data back over network 1180 to reader 1140. For example, application 1190 may signal a reader 1140 if any changes to pressure are detected. Alternatively, application 1190 may send messages to trigger reader 1140 to interrogate RFID/sensor 1120 for a measurement.

Application 1190 may be coupled to a database of RFID identification numbers 1196. When data is received from an RFID chip (via a reader), the application 1190 must associate the received identifier with a patient. Records in database 1196 may provide this mapping. For example, when a patient leaves a healthcare facility, the identifier of his or her RFID chip is associated with the patient name in database 1196.

Application 1190 may further be coupled to an electronic medical records database 1192. When patient data is processed by application 1190, application 1190 may forward the processed data to electronic medical records database 1192 via a protocol such as HL7.

Application 1190 may be further integrated with a remote patient monitoring station 1194. A healthcare provider monitors the data received from remote compartment monitoring devices to determine if additional medical intervention is necessary. When available, application 1190 provides patient monitoring station 1194 with location information. Application 1190 may display historical data or trends for monitoring station 1194.

Extensive testing has shown that the current RFID reader chips made for cell phones (for example, Near Field Communication ("NFC") chips based on ISO 15693 standards) are not well suited to read complex RFID sensors due to timing and/or power issues. The readers are essentially meant to read identification (ID) numbers and have a very short interrogation/response cycle time. Furthermore when the technology is passive (as is the case for most RFID) substantial power fluctuations occur on the RFID chip and this affects sensor accuracy.

Therefore medical grade sensors that require complex processing, power or accuracy will not work reliably with current RFID cell phones combined with standard passive RFID chip technology. In order to resolve this and to allow RFID cell phones to read the orthopedics skin patch comprising a complex MEMS sensor a modified RFID chip is required. This modified chip includes a serial peripheral interface (SPI) port and allows pre-processed sensor data to be stored in memory directly linked to the ID interrogation process of the RFID tag. This type of RFID tag therefore serves as a low cost "pass-through" radio. This design and method allows any sensor to be connected to common RFID technology and be read directly with current RFID enabled cell phones. The technology can be adapted to ISO 15693 tags for example and is directly compatible with multiprotocol 13.56 MHz RFID reader chips for cell phones such as the PN 544 C2 reader chip made by NXP.

Figure 12:
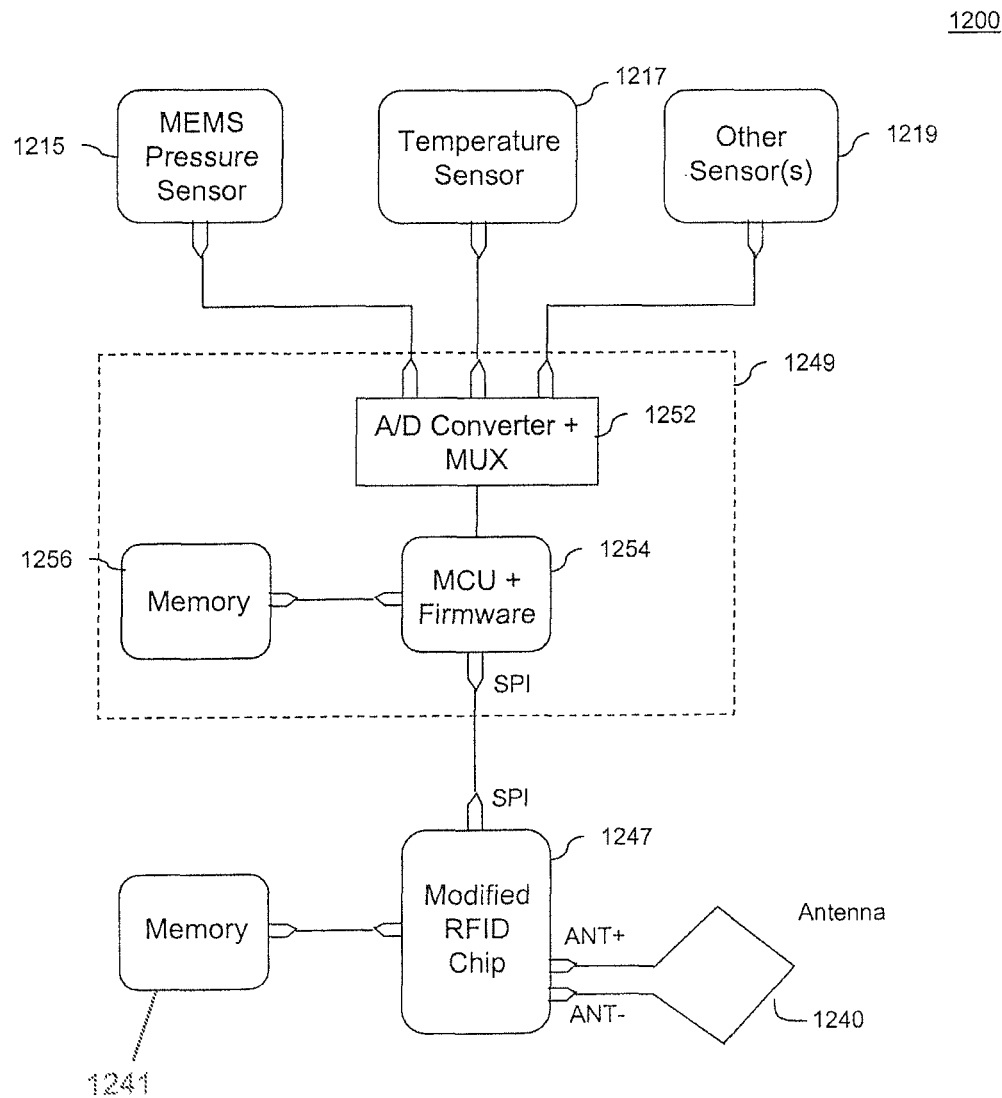
FIG. 12 depicts an exemplary system having a modified RFID chip, according to embodiments of the present invention.

Different circuit designs and options are possible for the pass through method. FIG. 12 depicts an exemplary system 1200 having a modified RFID chip, according to embodiments of the present invention. FIG. 12 illustrates how complex sensors can be handled using a passive modified RFID radio, where the processed sensor data is passed through the RFID part as part of the standard interrogation—transmission of RFID data. The system 1200 includes a plurality of external sensors, including temperature sensor 1217 and other sensor(s) 1219. In embodiments, the plurality of external sensors includes a complex calibrated external MEMS sensor 1215 and an ultra precise external thermistor to allow medical grade combined pressure and temperature sensor measurements.

Each of the plurality of external sensors is coupled to a sensor interface 1249. Sensor interface 1249 includes an analog to digital converter (ADC) and multiplexer 1252, an external microprocessor (MCU) and firmware 1254, and memory 1256. Using an external microprocessor and firmware allows compression of complex sensor data and extremely fast passage of information via the RFID chip, well within the limits of current standard RFID reader chips. Sensor interface 1249 further includes an external power source (e.g. battery, energy harvesting, solar, chemical, motion, etc.) that also can include a reference voltage calibration circuit. In an embodiment, sensor interface 1249 is included in a separate chip.

Sensor interface 1249 antenna 1240, and memory 1241 are coupled to modified RFID chip 1247. The command set for the external MCU and firmware 1254 is passed through the RFID tag 1247. The memory on the RFID chip is cleared either when full or bumped with each new interrogation or sensor data download or by external command from the RFID interrogator (cell phone).

The RFID chip 1247 and sensor interface 1249 of FIG. 12 can be integrated into a single hybrid chip, whereby the packaged sensor data is placed in memory and where the main processor would be powered by the external power source and the communication part built to handle the constraints imposed by current RFID interrogators. Alternatively, the components of sensor interface 1249 may be included in a separate integrated circuit chip.

Various designs are possible for the fully integrated chip. The system of FIG. 12 illustrates the combination of external temperature sensor 1217 and external MEMS sensor 1215. For temperature on chip a single calibration point digital sensor is preferred. Such sensor technology is described in U.S. Pat. No. 7,461,972 that is included by reference in its entirety.

Figure 13:
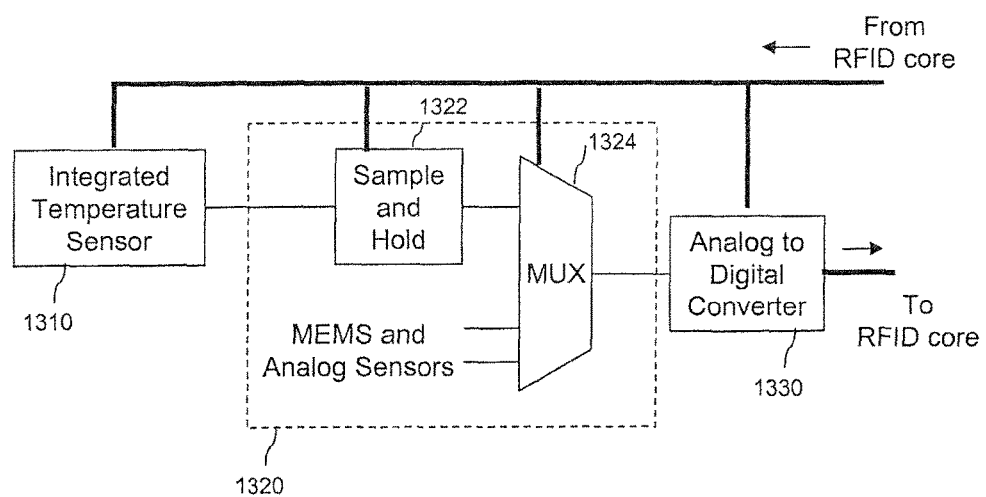
FIG. 13 is a block diagram illustrating a portion of an RFID device in accordance with an embodiment presented herein.

FIG. 13 is a block diagram illustrating a portion 1300 of an RFID device in accordance with an embodiment presented herein. Portion 1300 illustrates an integrated temperature sensor 1310, sensor interface 1320, and an analog to digital converter (ADC) 1330. Sensor interface 1320 receives data from integrated sensor 1310 and one or more external sensors. In an embodiment, integrated sensor data is fed into a sample and hold circuit 1322. The output of the sample and hold circuit 1322 and data from external sensors are fed into a multiplexer 1324. The output of multiplexer 1324 is fed into ADC converter 1330. The output of ADC 1330 is communicated to RFID core (not shown). RFID core may also communicate commands to the integrated sensor 1310, sensor interface 1320, and/or ADC 1330. Additionally, power may be provided to these components by RFID core.

Figure 14:
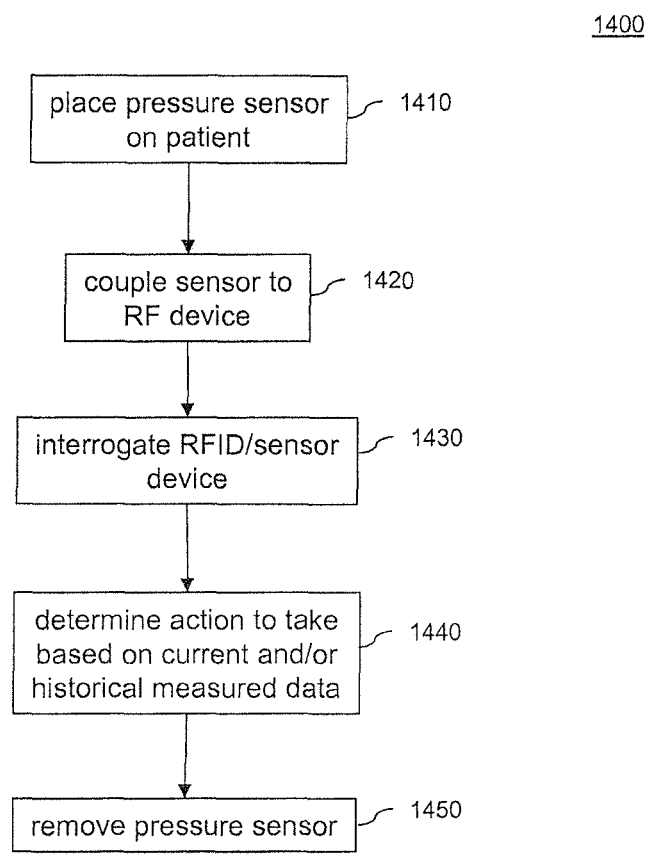
FIG. 14 is a flowchart illustrating a method of monitoring compartment pressure, according to embodiments of the present invention.

FIG. 14 is a flowchart 1400 illustrating a method of monitoring compartment pressure, according to embodiments of the present invention. Flowchart 1400 is discussed with reference to the embodiments of FIGS. 1 through 13. However, flowchart 1400 is not limited to those embodiments.

In step 1410, a pressure sensor is placed on a patient. In an embodiment, the pressure sensor is loaded on a needle or trocar. The needle or trocar is then inserted into the compartment. The needle or trocar is then removed leaving the sensor implanted in the compartment. In an alternate embodiment, a vessel such as the bulb or sac of FIG. 2 is placed into a compartment and coupled to a pressure sensor on the surface of the skin of the patient.

In step 1420, the pressure sensor is coupled to an RF device including an RFID chip. As described in the embodiments above, the RF device may be integrated in a patient bandage.

In step 1430, the RF device is interrogated by an RFID/sensor reader. In response to the interrogation signal, the RF device communicates the measured sensor (pressure) data to the RFID/sensor reader. RFID/sensor reader may process the received data or simply pass through the received data to an external application such as an application at a healthcare provider.

In step 1440, the RFID/sensor reader or application determines an action to take based on the current and/or historical measured pressure data. Example actions include generating and displaying a graph of the pressure over time, writing pressure information to medical records, and/or paging a healthcare provider if the current measured pressure is out of range or the pressure trend indicates pressure trending in an adverse direction.

In step 1450, after the period for monitoring has ended, the pressure sensor is removed. If the sensor was inserted into a compartment of the patient, the sensor is removed by pulling on the wire tether. If a vessel was inserted into the compartment (as described in FIG. 2), the vessel is removed by a healthcare provider.

Figure 15:
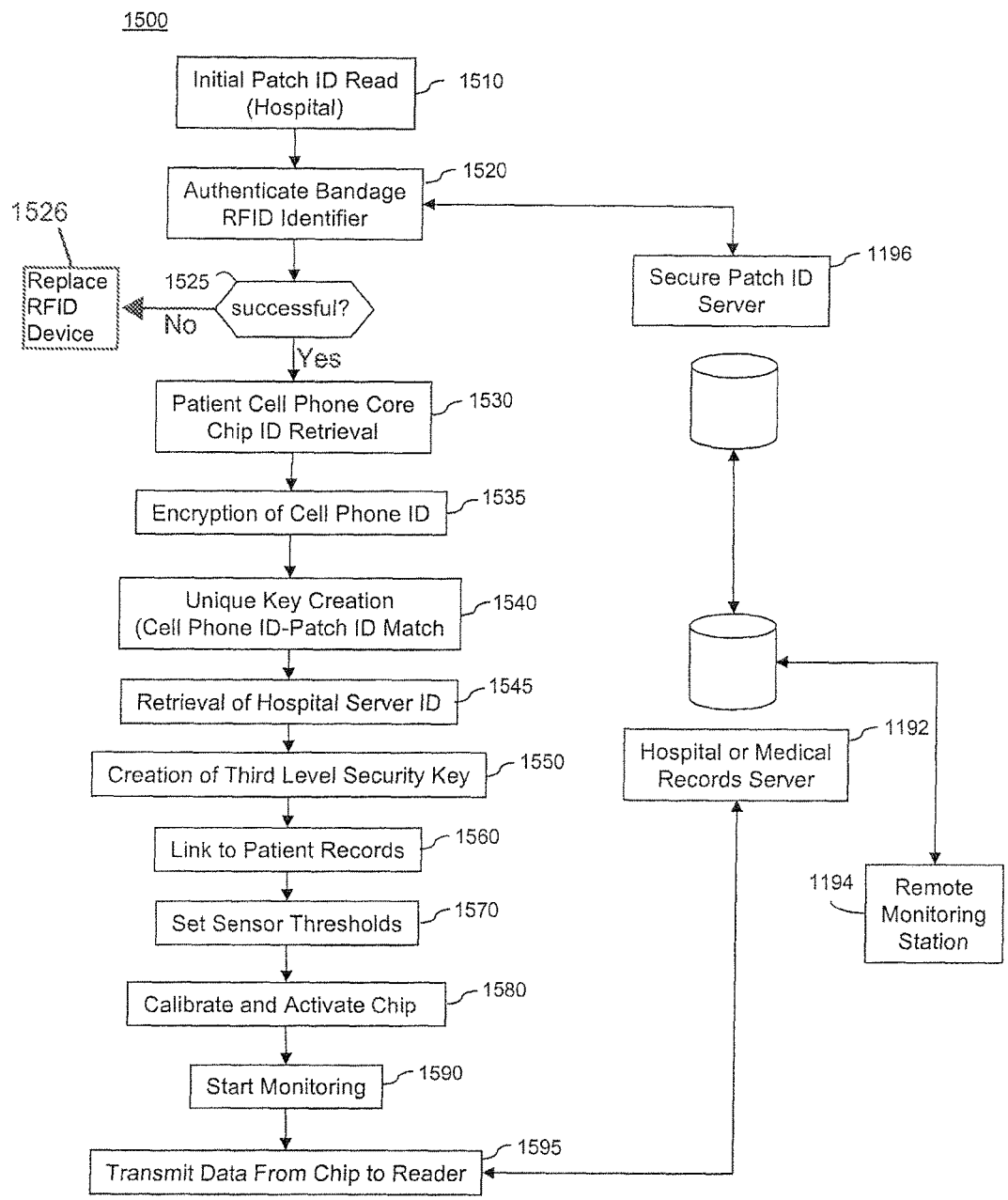
FIG. 15 is a flowchart showing a method for linking identifiers to create transparent and secure wireless monitoring of compartment syndrome in a patient, according to embodiments of the present invention.

FIG. 15 is a flowchart 1500 showing a method for linking identifiers to create transparent and secure wireless monitoring of compartment syndrome in a patient, according to embodiments of the present invention. Flowchart 1500 is described with reference to the embodiments described above. However, flowchart 1500 is not limited to those embodiments.

Prior to step 1510, a pressure sensor and associated RFID device is affixed via a bandage to a patient. In step 1510, an RFID reader at the healthcare provider performs an initial read of the RFID device.

In step 1520, the identifier of the bandage RFID is authenticated against a list of known bandage RFID identifiers stored in a local database. In an embodiment, the bandage RFID identifier is authenticated against a database of valid identifiers. The bandage RFID identifier, for example, may be validated against a list of identifiers for a given manufacturer, a medical facility (e.g., hospital), a unit within a medical facility, or a system level basis (e.g., a collection of hospital).

In step 1525, a determination is made whether the authentication is successful. If the authentication was not successful, the RFID device is replaced (step 1526). If authentication is successful, the process continues to step 1530.

In step 1530, the identifier of the RFID reader of the patient is retrieved. For example, the patient may have a cell phone with an integrated RFID reader. Alternatively, the healthcare facility may provide the patient with an RFID reader.

In step 1535, the identifier of the RFID reader is encrypted.

In step 1540, a second level cryptographic key is generated using the RFID reader identifier and the identifier of the bandage RFID chip.

In step 1545, the identifier of the healthcare facility is retrieved.

In step 1550, a third level security key is generated using the retrieved identifier of the healthcare facility.

In step 1560, the bandage RFID chip identifier and RFID reader identifier is linked to the patient and the patient record.

In step 1570, sensor thresholds within the RFID chip and associated pressure sensor are set.

In step 1580, the RFID chip is calibrated and activated.

In step 1590, compartment pressure monitoring begins.

In step 1595, data is transmitted from the RFID chip via RFID reader to an application. The transmitted data may be encrypted with one of the security keys created in step 1540 or 1550. For example, data may be transmitted to a records server and/or monitoring application at the medical facility. The medical facility can then detect changes to the status of the patient and intervene when necessary.

Figure 16:
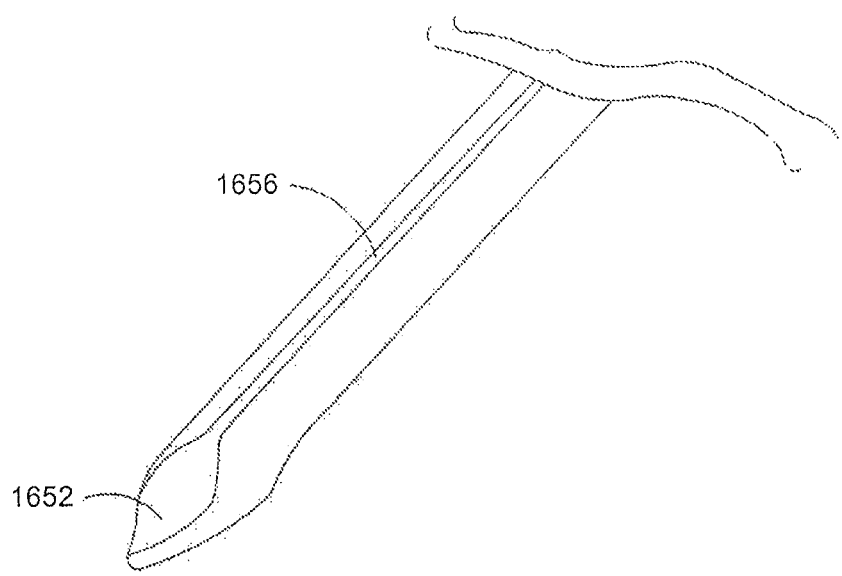
FIG. 16 is an exemplary embodiment of a needle used in accordance with an embodiment of the present invention.

FIG. 16 is an exemplary embodiment of a needle 1650 used in accordance with an embodiment of the present invention. The needle will break in half lengthwise to assist with insertion of the device 1652 into the skin. The needle has a very fine cut completely through its mid diameter—longitudinally. The two halves of the needle are held together by a plastic endcap (not shown) for attachment to a syringe. The plastic endcap is scored, and once the device 1652 placed into the tissue and the needle pulled out of the skin, the needle can be split in half to remove it from the lead wire (or tube) 1656 that is left in the tissue. This configuration allows for the sensor to be placed as an assembled unit, without requiring the skin patch or some fitting on the tether to pass through the insertion needle once the sensor is secured in the tissue.

Figure 17:
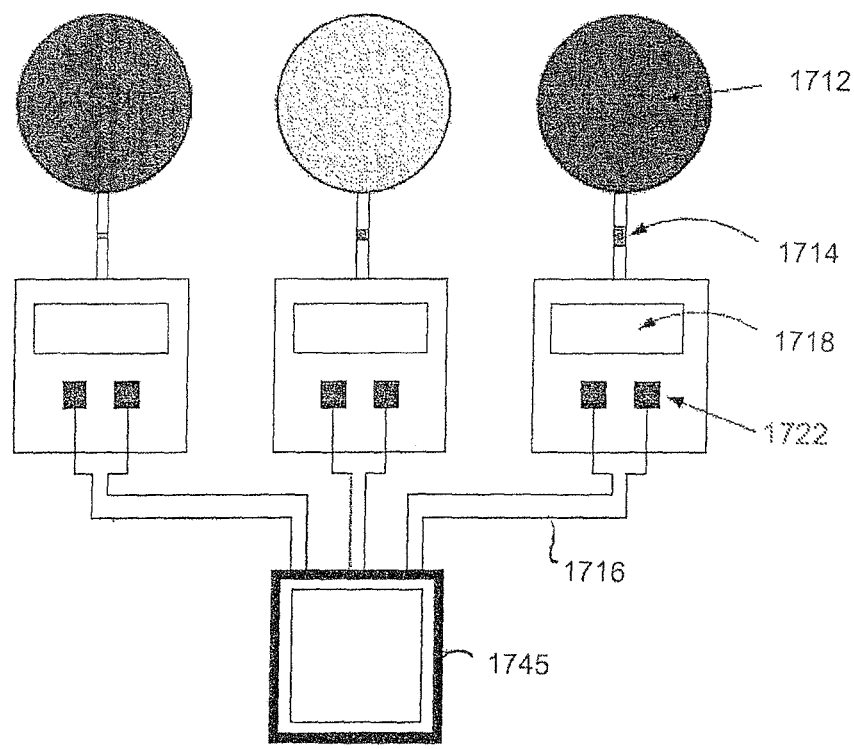
FIG. 17 is a schematic view of an opto-electronic compartment monitor in accordance with an alternative embodiment presented herein.

FIG. 17 is a schematic view of a low cost digital opto-electronic compartment monitor in accordance with an alternative embodiment presented herein. The opto-electronic compartment monitor of FIG. 17 may be used in applications where wireless devices or RFID readers are not available such as military or field applications.

Opto-electronic compartment monitor 1710 includes a plurality of color coded fluid cells 1712. In one embodiment, fluid cells are color coded, in other embodiments color is optional. Each color coded fluid cell 1712 is coupled through a pressure sensitive valve 1714 to a digital sensor 1722. When the pressure within the color coded fluid cell 1712 exceeds that of the pressure sensitive valve 1714 fluid flows into a digital sensor 1722 making the component conductive. The digital sensor 1722 thus acts as an on/off switch to send information through wires 1716 from device 1745. An optical window 1718 can be used optionally. A healthcare provider can then visually inspect the monitor to determine the status of the compartment pressure.

What is claimed is:

1. A method for monitoring pressure within a muscle fascia compartment of a patient, comprising:
   inserting a fluid-filled bulb through the patient's skin into an interior of the muscle fascia compartment of the patient,
   wherein the fluid-filled bulb is fluidly coupled by a fluid-filled tube extending through the patient's skin to a pressure sensor, and wherein the pressure sensor is coupled to a skin patch removably attached to the patient's skin by an adhesive;
   measuring pressure data within the muscle fascia compartment by the pressure sensor; and
   receiving and storing the measured muscle fascia compartment pressure data from the pressure sensor by a radio-frequency identification (RFD device coupled to the pressure sensor and the skin patch.

2. The method of claim 1, wherein inserting the fluid-filled bulb into the muscle fascia compartment comprises inserting the fluid-filled bulb into a leg of the patient.

3. The method of claim 2, wherein inserting the fluid-filled bulb into the leg of the patient comprises inserting the fluid-filled bulb into one of the anterior, lateral, deep posterior, and superficial posterior lower leg compartment of the patient.

4. The method of claim 1, wherein inserting the fluid-filled bulb into the muscle fascia compartment comprises inserting the fluid-filled bulb through a needle penetrating through the patient's skin and into the muscle fascia compartment.

5. The method of claim 1, further comprising interrogating the RFID device with a wireless RFID reader and communicating the measured muscle fascia compartment pressure data to the wireless RFID reader.

6. The method of claim 1, wherein measuring the pressure data within the muscle fascia compartment comprises continuously measuring the pressure data within the muscle fascia compartment.

7. The method of claim 1, wherein measuring the pressure data within the muscle fascia compartment comprises measuring the pressure data within the muscle fascia compartment for more than twenty-four hours.

8. The method of claim 1, further comprising transferring the measured muscle fascia compartment pressure data to a computing system.

9. The method of claim 8, further comprising the computing system calculating trends in the measured muscle fascia compartment pressure data over time.

10. The method of claim 9, further comprising alerting a healthcare provider in response to a determination that the measured muscle fascia compartment pressure data is outside a predetermined range or in response to a determination that the pressure trend indicates pressure trending in an adverse direction.

11. The method of claim 1, further comprising removing the fluid-filled bulb from the muscle fascia compartment through the patient's skin.

12. A system for monitoring pressure within a muscle fascia compartment of a patient, the system comprising:
   a skin patch comprising an adhesive substrate configured to removably affix the skin patch to the patient's skin;
   a fluid pressure sensor housed within the skin patch and configured to measure muscle fascia compartment pressure data;
   a radio-frequency identification (RFID) device housed within the skin patch and coupled to the pressure sensor, wherein the RFID device is configured to receive and store the muscle fascia compartment pressure data;
   a fluid-fillable bulb configured to be inserted through the patient's skin and into the muscle fascia compartment; and
   a fluid-fillable tube configured to penetrate through the patient's skin to fluidly couple the fluid-filled bulb implanted within the muscle fascia compartment with the pressure sensor housed within the skin patch.

13. The system of claim 12, wherein the muscle fascia compartment is in a leg of the patient.

14. The system of claim 12, wherein the bulb, tube, and pressure sensor of the system are configured such that an increase in pressure on the bulb within the muscle fascia compartment forces fluid into the tube and is registered at the pressure sensor housed within the skin patch.

15. The system of claim 12, further comprising a wireless RFID reader, wherein the RFID device is configured to transmit the stored muscle fascia compartment pressure data to the wireless RFID reader upon interrogation by the wireless RFID reader.

16. The system of claim 15, wherein the wireless RFID reader comprises one of a cell phone, a personal digital assistant, and a laptop computer.

17. The system of claim 15, wherein the wireless RFID reader is configured to process the muscle fascia compartment pressure data.

18. The system of claim 15, wherein the wireless RFID reader is configured to transfer the muscle fascia compartment pressure data to a computing system, wherein the computing system is configured to process the muscle fascia compartment pressure data, and wherein the computing system is configured to record and display trends in the muscle fascia compartment pressure data over time.

19. The system of claim 12, wherein the fluid pressure sensor and the RFID device are housed between an upper layer and the adhesive substrate of the skin patch.

20. A compartment syndrome monitoring system, comprising:
   a fluid-fillable bulb configured to be implanted within a compartment of a muscle group in a leg surrounded by fascia;
   a fluid-fillable tube coupled to the implantable fluid-fillable bulb and configured to penetrate through the skin of the leg to an exterior of the leg;
   a fluid pressure sensor configured to be disposed exterior to the skin of the leg and coupled to the fluid-fillable bulb by the fluid-fillable tube;
   an adhesive bandage configured to be coupled to the skin of the leg and the fluid pressure sensor;
   a radio-frequency identification (RFID) device coupled to the fluid pressure sensor and the adhesive bandage and configured to record fluid pressure data measured by the fluid pressure sensor from the fluid-fillable bulb within the compartment of the muscle group in the leg;
   an RFID reader configured to interrogate the RFID device to receive the recorded fluid pressure data from the RFID device; and
   a computer system configured to:

receive from the RFID reader the recorded fluid pressure data measured by the fluid pressure sensor from the fluid-fillable bulb within the compartment of the muscle group in the leg;

record and display trends in the recorded fluid pressure data over time; and alert a healthcare provider in response to a determination that the recorded fluid pressure data is outside of predetermined range.

\* \* \* \* \*